United States Patent
Fondin et al.

(10) Patent No.: US 7,754,193 B2
(45) Date of Patent: Jul. 13, 2010

(54) REDUCING COMPOSITION FOR PERMANENTLY RESHAPING KERATIN FIBERS AND PERMANENT-RESHAPING PROCESS

(75) Inventors: Thomas Fondin, Taverny (FR); Anne Sabbagh, Rueil Malmaison (FR)

(73) Assignee: L'Oreal S.A., Paris (FR)

( * ) Notice: Subject to any disclaimer, the term of this patent is extended or adjusted under 35 U.S.C. 154(b) by 1016 days.

(21) Appl. No.: 10/847,320

(22) Filed: May 18, 2004

(65) Prior Publication Data

US 2005/0112076 A1 May 26, 2005

Related U.S. Application Data

(60) Provisional application No. 60/477,729, filed on Jun. 12, 2003.

(30) Foreign Application Priority Data

May 19, 2003 (FR) .................. 03 05971

(51) Int. Cl.
*A61Q 5/04* (2006.01)
*A61Q 5/00* (2006.01)

(52) U.S. Cl. .................. 424/70.2; 424/70.1

(58) Field of Classification Search ........... None
See application file for complete search history.

(56) References Cited

U.S. PATENT DOCUMENTS

| | | | |
|---|---|---|---|
| 2,708,940 A | 5/1955 | De Mytt et al. | |
| 3,847,165 A | 11/1974 | Patel et al. | |
| 4,197,865 A | 4/1980 | Jacquet et al. | |
| 4,381,919 A | 5/1983 | Jacquet et al. | |
| 4,608,250 A | 8/1986 | Jacquet et al. | |
| 5,009,813 A | 4/1991 | Watanabe et al. | |
| 5,700,455 A | 12/1997 | Hinterwaldner et al. | |
| 5,932,201 A | 8/1999 | de Labbey et al. | |
| 6,022,836 A * | 2/2000 | Dubief et al. | 510/122 |
| 6,024,949 A | 2/2000 | Rose | |
| 6,303,110 B1 | 10/2001 | Maubru et al. | |
| 2003/0118537 A1 | 6/2003 | Devin-Baudoin et al. | |

FOREIGN PATENT DOCUMENTS

| | | |
|---|---|---|
| EP | 0 712 623 A2 | 5/1996 |
| GB | 2 026 052 A | 1/1980 |
| JP | A-09-301837 | 11/1997 |

OTHER PUBLICATIONS

Petrucchi and Harwood "General Chemistry Principles and Modern Applications" 6 ed 1993.*
English language Derwent Abstract of DE 199 02 246 A1, Dec. 9, 1999.
English language Derwent Abstract of DE 198 40 190 A1, Mar. 9, 2000.
English language Derwent Abstract of FR 2 514 640, Apr. 22, 1983.
English language Derwent Abstract for JP 09-071518.
English language Derwent Abstract for JP 09-301837.
English language abstract of JP 8 231 355 from Patent Abstracts of Japan.
French Search Report for FR 03 05971 (Priority Application for U.S. Appl. No. 10/847,320) dated Feb. 11, 2004.

* cited by examiner

*Primary Examiner*—Eric E. Silverman
(74) *Attorney, Agent, or Firm*—Finnegan, Henderson, Farabow, Garrett & Dunner

(57) ABSTRACT

The present disclosure relates to a composition for permanently reshaping keratin fibers, such as the hair, comprising ammonium bicarbonate and at least one other alkaline agent chosen from aqueous ammonia and ammonium salts other than ammonium bicarbonate, with an ammonium molar concentration ratio of greater than 2.1, at least one non-cyclic cationic polymer, and at least one reducing agent, wherein, when aqueous ammonia is present, it is present in an amount of less than 3% by weight. Also disclosed herein is permanent-reshaping process comprising the application of this reducing composition in a first stage, followed, after a leave-in time, by the application of a fixing composition and rinsing of the keratin fibers thus treated.

The present disclosure further relates to a multi-compartment device or kit comprising this reducing composition.

23 Claims, No Drawings

REDUCING COMPOSITION FOR PERMANENTLY RESHAPING KERATIN FIBERS AND PERMANENT-RESHAPING PROCESS

This application claims benefit of U.S. Provisional Application No. 60/477,729, filed Jun. 12, 2003.

The present disclosure relates to a reducing composition for permanently reshaping keratin fibers, such as the hair, to a permanent-reshaping process using this reducing composition, and to a multi-compartment device or "kit."

For the purposes of the present disclosure, the term "permanent-reshaping process" means any process for the long-lasting shaping or curling of the hair.

In the field of permanent reshaping of the hair, it is known practice to perform, on hair that has been placed under tension beforehand using rollers, curlers or the like, the opening of the disulphide bonds of cystine of the keratin using a composition comprising a reducing agent, and then, generally after rinsing the head of hair, to reconstitute the disulphide bonds by applying a composition, which is generally an oxidizing composition, which allows the style to be fixed. This technique thus can make it possible either to make the hair wavy, or to relax it, or to crimp it. The new shape given to the hair by a chemical treatment as described above can be long-lasting and may be able to withstand the action of washing with water or shampoo, as opposed to simple standard techniques of temporary reshaping, such as hairsetting.

Reducing compositions for permanently reshaping the hair can comprise, in the majority of cases, agents that can cause damage to hair that has already been sensitized or dyed, despite the presence of conditioners in these compositions. It may be necessary on this type of hair to use a pre-lotion in order to preserve the integrity of the hair by slowing down the penetration of the reducing agent. Unfortunately, these pre-lotions can have the effect of reducing the performance qualities of permanent-waving results in terms of curliness and liveliness.

Thus, it would be desirable to improve the techniques of permanent reshaping on hair that has already been sensitized or dyed, for example, by overcoming the above problems.

More specifically, there is a real need to provide a process for performing a permanent-reshaping operation, which gives lively reshaping, curls or crimps to hair that has already been sensitized or dyed, while at the same time maintaining good cosmetic qualities such as softness or disentangling and also preserving the artificial coloration of the hair when it has already been dyed.

It has been discovered that it is possible to solve at least one of the problems described above by using a reducing composition comprising a defined molar concentration ratio of ammonium, a defined aqueous ammonia content and at least one certain polymer.

Another aspect of the present disclosure concerns a process for permanently reshaping keratin fibers, such as the hair, comprising the application of the above-mentioned composition to the keratin fibers.

Yet another aspect of the present invention concerns a multi-compartment device or kit comprising at least one reducing composition as disclosed herein.

Other subjects, characteristics, aspects and advantages of the present disclosure will emerge even more clearly upon reading the description and the various examples that follow.

The process of the present disclosure may be applied to any keratin material in general, for instance, eyelashes, moustaches, body hair and other hairs.

The reducing compositions of the present disclosure for permanently reshaping keratin materials, such as the hair, comprise:

ammonium bicarbonate and at least one other alkaline agent chosen from aqueous ammonia and/or ammonium salts other than ammonium bicarbonate, such that these compositions have a molar concentration ratio R defined by the following formula:

$$R = \frac{\text{total number of moles of ammonium} - \text{number of moles of ammonium bicarbonate}}{\text{number of moles of ammonium bicarbonate}}$$

wherein R is greater than 2.1,
at least one non-cyclic cationic polymer, and
a reducing agent, wherein, when aqueous ammonia is present, it is present in a proportion of less than 3%, expressed as $NH_4OH$, by weight relative to the total weight of the composition.

For example, the at least one other alkaline agent may be aqueous ammonia.

For further example, the aqueous ammonia content may range from 1 to 3, such as from 1.5 to 3 by weight, relative to the total weight of the composition.

In one aspect of the present disclosure, the ratio R may range from 2.1 to 5, such as from 2.1 to 3.

In the ratio R, the total number of moles of ammonium comprises:

the number of moles of ammonium required to neutralize the thiol,
the number of moles of ammonium in excess, and
the number of moles of ammonium bicarbonate.

Among the optional additional alkaline agents that may be used, non-limiting mention may be made of monoethanolamine, triethanolamine and 1,3-diaminopropane derivatives.

Without being bound by theory, it appears that the equilibrium between the alkaline agents and the optimization of the ammonium bicarbonate concentration of this composition makes it possible to improve the performance qualities in terms of curliness, liveliness of the curls and cosmetic quality on sensitized hair, compared with reducing compositions of the prior art.

For the purposes of the present disclosure, the term "non-cyclic cationic polymer" means any polymer comprising cationic groups and/or groups that may be ionized into cationic groups, with the exception of those whose cationic charge is borne by a nitrogen atom contained in a ring.

The non-cyclic cationic polymers that may be used in accordance with the present disclosure may be chosen from all those already known per se as improving the cosmetic properties of the hair, for example, those described in the patent application EP-A-337,354 and in the French Patents FR-2,270,846, 2,383,660, 2,598,611, 2,470,596 and 2,519,863.

The non-cyclic cationic polymers that may be used, for example, include those chosen from non-cyclic cationic polymers comprising units comprising primary, secondary, tertiary and/or quaternary amine groups, which may either form part of the main polymer chain or may be borne by a side substituent directly attached thereto.

The non-cyclic cationic polymers that may be used herein have a number-average molecular mass ranging from 500 to $5 \times 10^6$, such as ranging from $10^3$ to $3 \times 10^6$.

Among the non-cyclic cationic polymers that may be used, non-limiting mention may be made, for example, of polymers of the polyamine, polyamino amide and polyquaternary ammonium type, such as those described in French Patent Nos. 2,505,348 and 2,542,997, for instance.

Further among the non-cyclic cationic polymers, non-limiting mention may be made of:

(1) Homopolymers or copolymers derived from acrylic or methacrylic esters or amides and comprising at least one of the units of formulae (42), (43), (44) and (45):

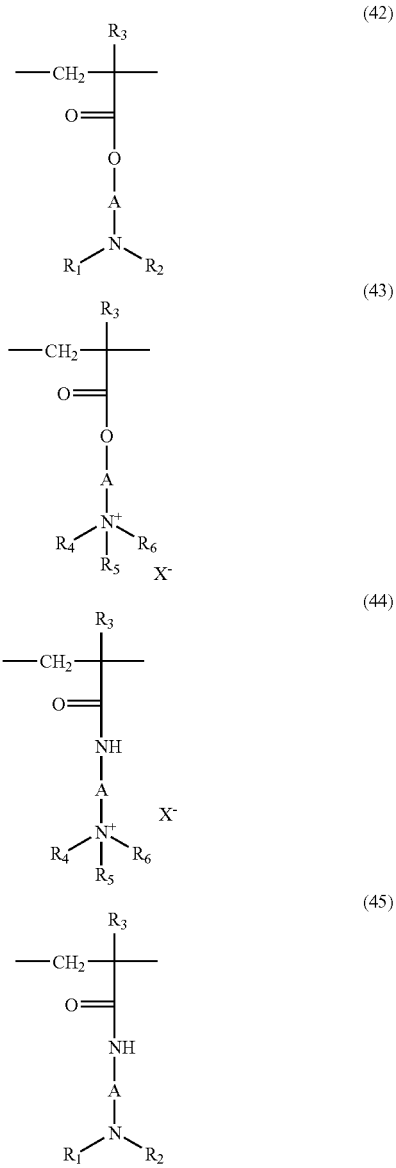

wherein:
- $R_3$ is chosen from hydrogen atoms and $CH_3$ radicals;
- A is chosen from linear and branched alkyl groups comprising from 1 to 6 carbon atoms, such as from 2 to 3 carbon atoms, and hydroxyalkyl groups ranging from 1 to 4 carbon atoms;
- $R_4$, $R_5$ and $R_6$, which may be identical or different, are chosen from alkyl groups comprising from 1 to 6 carbon atoms;
- $R_1$ and $R_2$, which may be identical or different, are chosen from hydrogen atoms and alkyl groups comprising from 1 to 6 carbon atoms, for instance, methyl and ethyl groups;
- X is chosen from anions derived from inorganic and organic acids, such as a methosulphate anion, and halides such as chloride or bromide.

The polymers of category (1) can also comprise at least one unit derived from comonomers that may be chosen from the family of acrylamides, methacrylamides, diacetone acrylamides, acrylamides and methacrylamides substituted on the nitrogen with an entity chosen from lower ($C_1$-$C_4$) alkyls, acrylic and methacrylic acids and esters thereof, and vinyl esters.

Thus, among the polymers of category (1), non-limiting mention may be made of:
- copolymers of acrylamide and of dimethylaminoethyl methacrylate quaternized with dimethyl sulphate or with a dimethyl halide, such as the product sold under the name HERCOFLOC by the company Hercules,
- the copolymers of acrylamide and of methacryloyloxyethyltrimethylammonium chloride described, for example, in the patent application EP-A-080,976 and sold under the name BINA QUAT P 100 by the company Ciba Geigy,
- the copolymer of acrylamide and of methacryloyloxy-ethyltrimethylammonium methosulphate sold under the name RETEN by the company Hercules.

(2) Cellulose ether derivatives comprising quaternary ammonium groups, described in French Patent No. 1,492,597, for instance, polymers sold under the name "JR" (JR 400, JR 125 and JR 30M) or "LR" (LR 400 or LR 30M) by the company Union Carbide Corporation. These polymers are also defined in the CTFA dictionary as quaternary ammoniums of hydroxyethylcellulose that have reacted with an epoxide substituted with a trimethylammonium group.

(3) Cationic cellulose derivatives such as cellulose copolymers or cellulose derivatives grafted with a water-soluble quaternary ammonium monomer, and described, for example, in U.S. Pat. No. 4,131,576, such as hydroxyalkylcelluloses, for instance hydroxymethyl-, hydroxyethyl- or hydroxypropylcelluloses grafted, for instance, with a methacryloylethyltrimethylammonium, methacrylamidopropyltrimethylammonium or dimethyldiallylammonium salt. The commercial products corresponding to this definition include, for example, those sold under the names Celquat L 200 and Celquat H 100 by the company National Starch.

(4) Cationic polysaccharides described, for example, in U.S. Pat. Nos. 3,589,578 and 4,031,307, such as guar gums comprising cationic trialkylammonium groups. Guar gums modified with a salt (e.g., chloride) of 2,3-epoxypropyltrimethylammonium, may be used, for example. Such products are sold, for instance, under the trade names Jaguar C13 S, Jaguar C 15, Jaguar C 17 and Jaguar C162 by the company Meyhall.

(5) Water-soluble polyamino amides prepared, for example, by polycondensation of an acidic compound with a polyamine; these polyamino amides can be crosslinked with an epihalohydrin, a diepoxide, a dianhydride, an unsaturated dianhydride, a bis-unsaturated derivative, a bis-halohydrin, a bis-haloacyldiamine, a bis-alkyl halide, or alternatively, with an oligomer resulting from the reaction of a difunctional compound that is reactive with an entity chosen from bishalohydrin, bis-haloacyldiamine, bis-alkyl halide, epihalohydrin, diepoxide and bis-unsaturated derivatives; the crosslinking agent may be used in an amount ranging from 0.025 to 0.35 mol per amine group of the polyamino amide; these polyamino amides can be alkylated or, if they comprise at least one tertiary amine functions, they can be quaternized. Such polymers are described, for instance, in French Patent Nos. 2,252,840 and 2,368,508.

(6) Polyamino amide derivatives resulting from the condensation of polyalkylene polyamines with polycarboxylic acids followed by alkylation with difunctional agents. Mention may be made, for example, of adipic acid/dialkylamino-hydroxyalkyl-dialkylene-triamine polymers in which the alkyl radical comprises from 1 to 4 carbon atoms, such as methyl, ethyl and propyl radicals. Such polymers are described, for instance, in French Patent No. 1,583,363. Among these derivatives, non-limiting mention may be made, for example, of the adipic acid/dimethylamino-hydroxypropyl/diethylenetriamine polymers sold under the name "CARTARETINE F, F4 or F8" by the company Sandoz.

(7) Polymers obtained by reaction of a polyalkylene polyamine comprising two primary amine groups and at least one secondary amine group with a dicarboxylic acid chosen from diglycolic acid and saturated aliphatic dicarboxylic acids having from 3 to 6 carbon atoms. The molar ratio between the polyalkylene polyamine and the dicarboxylic acid ranges from 0.8:1 to 1.4:1; the polyamino amide resulting therefrom is reacted with epichlorohydrin in a molar ratio of epichlorohydrin relative to the secondary amine group of the polyamino amide ranging from 0.5:1 to 1.8:1. Such polymers are described for instance, in U.S. Pat. Nos. 3,227,615 and 2,961,347. Polymers of this type are sold in particular under the name "HERCOSETT 57" by the company Hercules Inc., or alternatively under the name "PD 170" or "DELSETTE 101" by the company Hercules in the case of the adipic acid/epoxypropyl/diethylenetriamine copolymer.

(8) Diquaternary ammonium polymers comprising repeating units corresponding to formula (48):

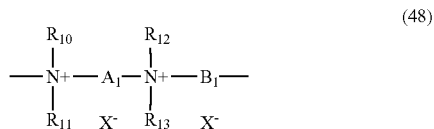

(48)

wherein:
$R_{10}$, $R_{11}$, $R_{12}$ and $R_{13}$, which may be identical or different, are chosen from alkyl and hydroxyalkyl radicals comprising from 1 to 4 carbon atoms; A1 and B1 are chosen from linear and branched, saturated and unsaturated polymethylenic groups comprising 2 to 20 carbon atoms, which may optionally comprise in the main chain at least one entity chosen from oxygen atoms, cyclic aromatic radicals, and sulphide, sulphoxide, sulphone, disulphide, amino, alkylamino, hydroxyl, quaternary ammonium, ureido, amido and ester groups.

$X^-$ is chosen from anions derived from inorganic and organic acids.

(9) Polyquaternary ammonium polymers comprising units of formula (50):

wherein:
p is an integer ranging from 1 to 6, D may be a bond or may be chosen from —$(CH_2)_r$—CO— groups wherein r is equal to 4 or 7, and $X^-$ is an anion derived from a mineral or organic acid.

The cationic polymers comprising units of formula (50) are described for example, in the patent application EP-A-122, 324, and may be prepared according to the processes described in U.S. Pat. Nos. 4,157,388; 4,390,689; 4,702,906; and 4,719,282.

Among the polymers of formula (50), non-limiting mention may be made of those with a molecular mass, measured by carbon-13 NMR, of less than 100,000, and in the formula of which:

p is equal to 3, and
a) D is chosen from —$(CH_2)_4$—CO— groups, X is a chlorine atom, the molecular mass measured by carbon-13 NMR ($^{13}$C NMR) being about 5600; a polymer of this type is sold by the company Miranol under the name MIRAPOL-AD1,
b) D is chosen from —$(CH_2)_7$—CO— groups, X is a chlorine atom, the molecular mass measured by carbon-13 NMR ($^{13}$C NMR) being about 8100; a polymer of this type is sold by the company Miranol under the name MIRAPOL-AZ1,
c) D is a bond, X is a chlorine atom, the molecular mass measured by carbon-13 NMR ($^{13}$C NMR) being about 25,500; a polymer of this type is sold by the company Miranol under the name MIRAPOL-A15,
d) a "Block Copolymer" formed from units corresponding to the polymers described in paragraphs a) and c), sold by the company Miranol under the names MIRAPOL-9 ($^{13}$C NMR molecular mass, about 7,800), MIRAPOL-175 ($^{13}$C NMR molecular mass, about 8,000) and MIRAPOL-95 ($^{13}$C NMR molecular mass, about 12,500).

For further example, the polymer comprising units of formula (50) wherein p is equal to 3, D is a bond, and X is a chlorine atom, the molecular mass measured by carbon-13 NMR ($^{13}$C NMR) being about 25,500, may also be used according to the present disclosure.

(10) Polyamines such as POLYQUART H sold by Henkel, which is given under the reference name "Polyethylene glycol (15) tallow polyamine" in the CTFA dictionary.

(11) Crosslinked methacryloyloxy($C_1$-$C_4$)alkyltri($C_1$-$C_4$)-alkylammonium salt polymers, such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound containing olefinic unsaturation, for instance, methylenebisacrylamide. A crosslinked acrylamide/methacryloyloxyethyltrimethyl-ammonium chloride copolymer (20/80 by weight) in the form of a dispersion comprising 50% by weight of the said copolymer in mineral oil can be also be used, for example. This dispersion is sold under the name "Salcare® SC 92" by the

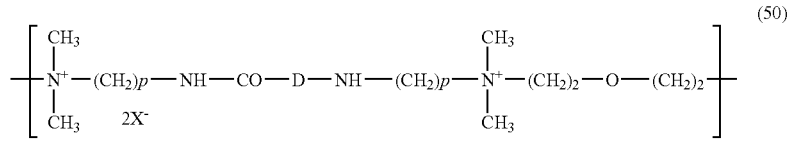

(50)

company Allied Colloids. A cross linked methacryloyloxy-ethyltrimethylammonium chloride homopolymer comprising about 50% by weight of the homopolymer in mineral oil or in a liquid ester can also be used. These dispersions are sold under the names "Salcare® SC 95" and "Salcare® SC 96" by the company Allied Colloids.

Other cationic polymers that can be used in the context of the present disclosure are polyalkyleneimines, such as polyethyleneimines, condensates of polyamines and of epichlorohydrin, quaternary polyureylenes and chitin derivatives.

Among all the non-cyclic cationic polymers that may be used according to the present disclosure, non-limiting mention may be made of the polymers of categories (1), (9) and (11), for example, the polymers comprising repeating units of formula (W):

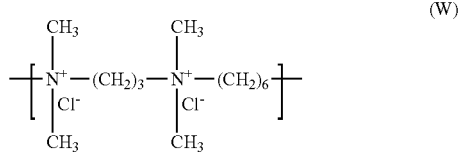

such as those with a molecular weight, determined by gel permeation chromatography, ranging from 9,500 to 9,900; and the polymers comprising repeating units of formula (U):

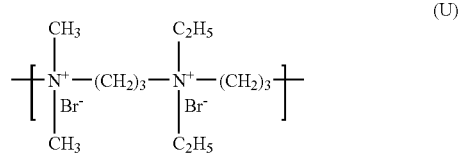

such as those with a molecular weight, determined by gel permeation chromatography, of 1,200.

The concentration of non-cyclic cationic polymer in the reducing composition may range from 0.01% to 20%, such as from 0.1% to 10%, relative to the total weight of the composition.

The reducing compositions of the invention comprise at least one reducing agent. This reducing agent may be chosen from alkali metals and alkaline-earth metal sulphites. For example, the reducing agent may be a thiol.

The thiol of the reducing composition may be chosen from thiols known as reducing agents, for instance thioglycolic acid, glyceryl or glycol monothioglycolate, cysteamine and its $C_1$-$C_4$ acyl derivatives such as N-acetylcysteamine or N-propionylcysteamine, cysteine, N-acetylcysteine, N-mercaptoalkylamides of sugars, such as N-(2-mercaptoethyl)gluconamide, 3-mercaptopropionic acid and its derivatives, thiolactic acid and its esters, such as glyceryl monothiolactate, thiomalic acid, pantethine, thioglycerol, the N-(mercaptoalkyl)-hydroxyalkylamides described in the patent application EP-A-354,835 and the N-mono- or N,N-dialkylmercapto-4-butyramides described in the patent application EP-A-368,763, the aminomercaptoalkylamides described in the patent application EP-A-432,000, the N-(mercaptoalkyl)-succinamic acid and N-(mercaptoalkyl)succinimide derivatives described in the patent application EP-A-465,342, the alkylaminomercaptoalkylamides described in the patent application EP-A-514,282, and the mixture of 2-hydroxypropyl thioglycolate and of 2-hydroxy-1-methylethyl thioglycolate described in the patent application FR-A-2,679,448.

Non-limiting mention may be made, for example, of thioglycolic acid, thiolactic acid, cysteine, cysteamine and salts thereof, and glyceryl thioglycolate.

For example, the thiol may be chosen from thioglycolic acid, cysteine and salts thereof.

The at least one reducing agent may be present in an amount ranging from 1% to 20% by weight, relative to the total weight of the reducing composition.

The pH of the reducing composition generally ranges from 6 to 10, such as from 7 to 9.

The reducing composition may be in a form chosen from thickened and non-thickened lotions, creams, gels, and any other suitable form, and may also comprise additives known for their use in reducing compositions for permanently reshaping the hair.

The reducing composition may also comprise a solvent, for instance ethanol, propanol, isopropanol or glycerol, at a maximum concentration of 20% relative to the total weight of the composition.

Another embodiment of the invention relates to a process for permanently reshaping keratin fibers, such as the hair, comprising:
  (i) applying a reducing composition as defined above to keratin material,
  (ii) after a leave-in time required for the reduction of the keratin material, optional rinsing the keratin material, and then applying a fixing composition,
  (iii) after a leave-in time required for fixing, rinsing the keratin material thus treated.

The keratin material may be placed under tension, for instance, using rollers, curlers or the like, before, during, or after the application of the reducing composition.

A pre-lotion may be applied to the keratin material before the application of the reducing composition. This pre-lotion may comprise an amino silicone.

The reducing composition may be applied to a moistened keratin material.

The leave-in time for the reducing composition onto a head of hair may range from 2 to 40 minutes, for example from 5 to 30 minutes, so as to give the reducing agent enough time to correctly act on the keratin material. This leave-in time generally takes place by leaving the treated head of hair at rest, either at room temperature or with heating.

The hair impregnated with the reducing composition may then be thoroughly rinsed, generally with water. Optionally, a phase of heating at high temperature for a few seconds is performed.

Next, an oxidizing composition is applied to the hair for the purpose of fixing the new shape given to the hair. It may also be envisaged to leave the hair to oxidize in the air.

This fixing composition may comprise any oxidizing agent known per se. For example, the fixing composition may comprise at least one oxidizing agent chosen from hydrogen peroxide, urea peroxide, alkali metal bromates and persalts such as perborates and persulphates.

The pH of the fixing composition may range from 2 to 10.

As in the case of the application of the reducing composition, the fixing composition may also have a leave-in time on the head of hair, which may range from 3 to 30 minutes, such as from 5 to 15 minutes.

In the final step of the process according to one embodiment of the present disclosure, the head of hair thus treated is rinsed after the leave-in time for the fixing composition ends.

Mechanical means, such as rollers, curlers, and the like, that may have held the hair under tension in the desired shape throughout the treatment are removed from the head of hair, either before or after rinsing out the fixing composition, the removal of the tensioning means possibly being followed by a new application of a certain amount of fixing composition.

The process is completed by natural drying or by any other means of drying, such as infrared, hair dryer, and the like, in order to obtain beautiful curls.

The fixing composition also contains pH regulators, so as to maintain an adequate pH.

The fixing or reducing compositions may also comprise, for example, at least one additive chosen from surfactants, silicones, waxes, thickeners, penetrating agents, fatty alcohols, lanolin derivatives, ceramides, active ingredients, agents for preventing hair loss, antidandruff agents, suspending agents, sequestering agents, opacifiers, stabilizers, dyes, silicone or non-silicone sunscreens, preserving agents, fragrances and dithio compounds.

According to the present disclosure, a head of hair that has good cosmetic properties is may be obtained, wherein the hair exhibits at least one property chosen from being shinier, softer and easier to disentangle and style. The hair may also have good qualities in terms of curliness and liveliness of the curls, even on sensitized hair.

Another embodiment of the invention relates to a multi-compartment device or kit for permanently reshaping keratin fibers, comprising at least one first compartment comprising at least one reducing composition as defined above, and at least one second compartment comprising at least one fixing composition.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

The disclosure may be understood more clearly with the aid of the non-limiting examples that follow, which constitute non-limiting embodiments of the process according to the present disclosure.

EXAMPLES OF COMPOSITIONS

A reducing composition (1) in accordance with the present disclosure was prepared:

| | |
|---|---|
| Thioglycolic acid | 7 g |
| Pentasodium salt of diethylenetriaminepenta-acetic acid | 0.4 g |
| Aqueous ammonia as an aqueous solution containing 20% $NH_3$ | 6.8 g |
| Ammonium bicarbonate | 2.5 g |
| Mexomere PO (Chimex)* | 1.6 g |
| Demineralized water | qs 100 g |

A reducing composition (2) in accordance with the present disclosure was prepared:

| | |
|---|---|
| Thioglycolic acid | 6.7 g |
| Pentasodium salt of diethylenetriaminepenta-acetic acid | 0.4 g |
| Aqueous ammonia as an aqueous solution containing 20% $NH_3$ | 6.5 g |
| Ammonium bicarbonate | 2.5 g |
| Mexomere PO (Chimex)* | 1.6 g |
| Demineralized water | qs 100 g |

*Non-cyclic cationic polymer of structure W as an aqueous solution

The fixing composition (3) outlined below was prepared:

| | |
|---|---|
| Hydrogen peroxide as a 50% solution | 4.8 g |
| Lauryldimethylamine oxide as an aqueous solution (30%) | 2.15 g |
| Merquat 100 | 1.25 g |
| Citric acid | 0.1 g |
| Demineralized water | qs 100 g |

Results of Head Tests by Comparing with a Permanent-Waving Product Dulcia Vital 2 (DV2) Sold by the Company L'Oréal I—With the Reducing Composition (1)

Composition (1) was applied to moistened hair rolled onto curlers, and left on for 10 minutes. On the other side, the DV2 reducing agent was applied for 10 minutes. After rinsing, fixing was performed with composition (3) and the DV2 fixer for 5 minutes before the final rinsing.

On all of the eight (8) models, the novel compositions gave moistened hair that was judged to be softer and easier to disentangle, with livelier curls, and on dried hair gave an improvement in its disentangling, softness and sheen.

Over time, better remanence of these cosmetic effects compared with the DV2 permanent-waving product were also observed.

Superpositions (3 applications) were performed, and marked superiority was obtained as regards all the curliness and cosmetic criteria compared with the DV2 permanent-waving product.

Results of Head Tests by Comparing with a Permanent-Waving Product Dulcia Vital 2 (DV2) Sold by the Company L'Oréal with an Optimiser Présifon 1 Prelotion Sold by the Company L'Oréal II—With the Reducing Composition (2)

The thioglycolic acid composition of composition (2) is equivalent to that of the reducing agent of the permanent-waving product DV2.

Composition (2) was applied to moistened hair rolled up on curlers, and left on for 10 minutes. To other moistened hair, the Optimiser Présifon 1 prelotion reducing agent was applied before rolling up on curlers, followed by the DV2 reducing agent for 10 minutes. After rinsing, fixing was performed with composition (3) and the DV2 fixer for 5 minutes before the final rinsing.

On all the models, the novel compositions give a more crimped head of hair with livelier curls, and on dried hair an improvement in the body for equivalent cosmetic qualities.

Over time, better remanence of these cosmetic effects compared with the permanent-waving product DV2 was observed.

Superpositions (3 applications) were performed, and the Applicant obtained marked superiority on all of the curliness and cosmetic criteria compared with the permanent-waving product DV2.

Effect on Dyeing

Locks of natural hair containing 90% white hairs that had been dyed with a dye Feria® 7.40 sold by L'Oréal, followed by a series of four shampoo washes, were then permanent-waved with the reducing compositions (1) and (2) and the DV2 reducing composition.

Less stripping-out of the color with the reducing composition (2) compared with the reducing composition (1) and the DV2 reducing composition was observed.

What is claimed is:

1. A reducing composition for permanently reshaping keratin fibers, comprising:
ammonium bicarbonate and at least one other alkaline agent chosen from aqueous ammonia and ammonium salts other than ammonium bicarbonate, such that these compositions have a molar concentration ratio R of the following formula:

$$R = \frac{\text{total number of moles of ammonium} - \text{number of moles of ammonium bicarbonate}}{\text{number of moles of ammonium bicarbonate}}$$

wherein the ratio R is greater than 2.1;
at least one non-cyclic cationic polymer chosen from polyamine and polyquaternary ammonium polymers chosen from polymers comprising the repeating units of formula (W):

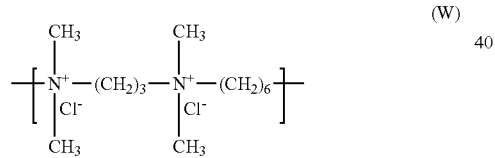

the molecular weight of which ranges from 9,500 to 9,900, and polymers comprising the repeating units of formula (U):

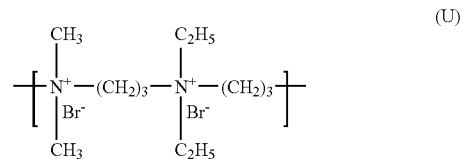

the molecular weight of which is about 1,200, and
at least one reducing agent;
wherein when aqueous ammonia is present, it is present in an amount less than 3%, expressed as $NH_4OH$, by weight relative to the total weight of the composition.

2. The reducing composition according to claim 1, wherein the keratin fibers are hair.

3. The reducing composition according to claim 1, wherein the ratio R ranges from 2.1 to 5.

4. The reducing composition according to claim 3, wherein the ratio R ranges from 2.1 to 3.

5. The reducing composition according to claim 1, wherein the at least one other alkaline agent is aqueous ammonia.

6. The reducing composition according to claim 5, wherein aqueous ammonia is present in an amount ranging from 1% to 3% by weight, relative to the total weight of the composition.

7. The reducing composition according to claim 6, wherein aqueous ammonia is present in an amount ranging from 1.5% to 3% by weight, relative to the total weight of the composition.

8. The reducing composition according to claim 1, wherein the at least one non-cyclic cationic polymer is present in the reducing composition in an amount ranging from 0.01% to 20% by weight, relative to the total weight of the composition.

9. The reducing composition according to claim 8, wherein the at least one non-cyclic cationic polymer is present in an amount ranging from 0.1% to 10% by weight, relative to the total weight of the composition.

10. The reducing composition according to claim 1, wherein the at least one reducing agent is chosen from sulphites and thiols.

11. The reducing composition according to claim 10, wherein the thiols are chosen from thioglycolic acid; thiolactic acid; cysteine, cysteamine and salts thereof; and glyceryl thioglycolate.

12. The reducing composition according to claim 1, further comprising at least one additive chosen from surfactants, silicones, waxes, thickeners, penetrating agents, fatty alcohols, lanolin derivatives, ceramides, active ingredients, agents for preventing hair loss, antidandruff agents, suspending agents, sequestering agents, opacifiers, stabilizers, dyes, silicone and non-silicone sunscreens, preserving agents, fragrances and dithio compounds.

13. A process for permanently reshaping keratin fibers, comprising:
i) applying to the keratin material a reducing composition comprising
ammonium bicarbonate and at least one other alkaline agent chosen from aqueous ammonia and ammonium salts other than ammonium bicarbonate, such that these compositions have a molar concentration ratio R of the following formula:

$$R = \frac{\text{total number of moles of ammonium} - \text{number of moles of ammonium bicarbonate}}{\text{number of moles of ammonium bicarbonate}}$$

wherein the ratio R is greater than 2.1,
at least one non-cyclic cationic polymer chosen from polyamine and polyquaternary ammonium polymers chosen from polymers comprising the repeating units of formula (W):

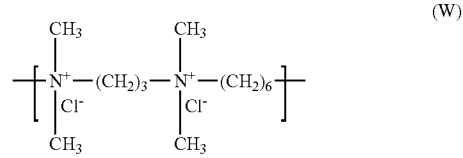

the molecular weight of which ranges from 9,500 to 9,900, and polymers comprising the repeating units of formula (U):

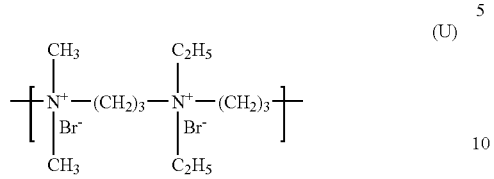

the molecular weight of which is about 1,200, and
at least one reducing agent,
wherein when aqueous ammonia is present, it is present in an amount less than 3%, expressed as $NH_4OH$, by weight relative to the total weight of the composition;
   ii) after a leave-in time required for the reduction of the keratin fibers, applying a fixing composition;
   iii) after a leave-in time required for fixing, rinsing the keratin fibers.

14. The process according to claim 13, wherein the keratin fibers are hair.

15. The process according to claim 13, wherein, prior to applying the fixing composition, the keratin fibers are rinsed.

16. The process according to claim 13, wherein the fixing composition comprises at least one oxidizing agent chosen from hydrogen peroxide, urea peroxide, alkali metal bromates and persalts.

17. The process according to claim 16, wherein the at least one persalt is chosen from perborates and persulphates.

18. The process according to claim 13, wherein a pre-lotion is applied to the keratin fibers before applying the reducing composition.

19. The process according to claim 18, wherein the pre-lotion comprises an amino silicone.

20. The process according to claim 13, wherein the reducing composition is applied to a moistened keratin fibers.

21. The process according to claim 13, wherein, before applying the fixing composition, the keratin fibers are heated at high temperature for a few seconds.

22. A multi-compartment kit for permanently reshaping keratin fibers, comprising
   at least one first compartment comprising at least one reducing composition comprising
      ammonium bicarbonate and at least one other alkaline agent chosen from aqueous ammonia and ammonium salts other than ammonium bicarbonate, such that these compositions have a molar concentration ratio R of the following formula:

$$R = \frac{\text{total number of moles of ammonium} - \text{number of moles of ammonium bicarbonate}}{\text{number of moles of ammonium bicarbonate}}$$

wherein the ratio R is greater than 2.1,
   at least one non-cyclic cationic polymer chosen from polyamine and polyquaternary ammonium polymers chosen from polymers comprising the repeating units of formula (W):

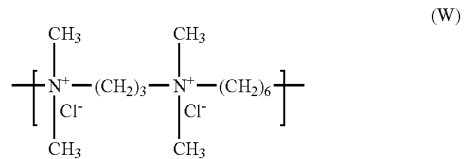

the molecular weight of which ranges from 9,500 to 9,900, and polymers comprising the repeating units of formula (U):

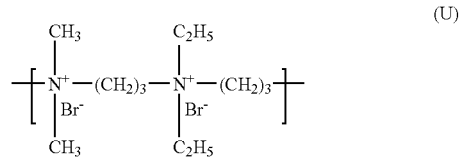

the molecular weight of which is about 1,200, and
at least one reducing agent,
wherein when aqueous ammonia is present, it is present in an amount less than 3%, expressed as $NH_4OH$, by weight relative to the total weight of the composition; and
   at least one second compartment comprising at least one fixing composition.

23. The multi-compartment kit according to claim 22, wherein the keratin fibers are hair.

* * * * *